United States Patent [19]

Ramakrishnan et al.

[11] Patent Number: 5,335,542
[45] Date of Patent: Aug. 9, 1994

[54] INTEGRATED PERMEABILITY MEASUREMENT AND RESISTIVITY IMAGING TOOL

[75] Inventors: T. S. Ramakrishnan, Bethel; David Rossi, Newtown; Yogesh Dave, Stamford; William Murphy, Redding, all of Conn.; Richard Plumb, Cambridge, England; Peter Goode, Rostrevor, Australia; Fikri Kuchuk, New Fairfield, Conn.; James Helwig, Dallas, Tex.; François M. Auzerais; Elizabeth B. Dussan V., both of Ridgefield, Conn.

[73] Assignee: Schlumberger Technology Corporation, New York, N.Y.

[21] Appl. No.: 16,933

[22] Filed: Feb. 12, 1993

Related U.S. Application Data

[63] Continuation-in-part of Ser. No. 761,213, Sep. 17, 1991, Pat. No. 5,269,180.

[51] Int. Cl.$^5$ .............. E21B 47/06; E21B 47/09; E21B 49/08; E21B 49/10
[52] U.S. Cl. .................. 73/152; 73/155; 166/250
[58] Field of Search ............ 73/152, 155, 153, 38; 166/250, 264; 175/48; 324/324, 325, 353

[56] References Cited

U.S. PATENT DOCUMENTS

| | | | |
|---|---|---|---|
| 2,747,401 | 5/1956 | Doll | 73/151 |
| 3,059,695 | 10/1962 | Barry et al. | 324/324 |
| 3,237,094 | 2/1966 | Blackburn et al. | 166/250 |
| 3,772,589 | 11/1973 | Scholberg | 324/10 |
| 4,251,773 | 2/1981 | Cailliau et al. | 324/347 |
| 4,420,975 | 12/1983 | Nagel et al. | 73/155 |
| 4,506,548 | 3/1985 | Zemanek, Jr. | 73/152 |
| 4,556,884 | 12/1985 | Howells et al. | 73/155 |
| 4,567,759 | 2/1986 | Ekstrom et al. | 73/152 |
| 4,594,552 | 6/1986 | Grimaldi et al. | 324/375 |
| 4,692,908 | 9/1987 | Ekstrom et al. | 367/27 |
| 4,716,973 | 1/1988 | Cobern | 166/250 |
| 4,742,459 | 5/1988 | Lasseter | 324/353 |
| 4,843,878 | 7/1989 | Purfurst et al. | 73/155 |
| 4,860,581 | 8/1989 | Zimmerman et al. | 73/155 |
| 4,890,487 | 1/1990 | Dussan V. et al. | 73/152 |
| 4,913,231 | 4/1990 | Muller et al. | 166/250 |
| 4,936,139 | 6/1990 | Zimmerman et al. | 73/155 |
| 5,036,283 | 7/1991 | Trouiller et al. | 324/375 |
| 5,159,978 | 11/1992 | Tomek et al. | 166/250 |

OTHER PUBLICATIONS

"Calculation of Relative Permeability from Displacement Experiments" by Johnson et al. Petroleum Transactions AIME 1959.
"A Laboratory Investigation of Permeability in Hemispherical Flow . . . " by Ramakrishnan et al. SPE 22689 1991, pp. 319–331.
"Formation Imaging with Microelectrical Scanning Arrays" by Ekstrom et al. SPWLA 27th Annual Logging Symposium 1986.

*Primary Examiner*—Hezron E. Williams
*Assistant Examiner*—George Dombroske
*Attorney, Agent, or Firm*—Leonard W. Pojunas; David P. Gordon

[57] ABSTRACT

A borehole tool having adjacently located fluid injection/withdrawal apparatus and an electromagnetic measurement apparatus is provided. The electromagnetic measurement apparatus can be an imaging apparatus for helping set the tool in desired locations for permeability testing via fluid injection or withdrawal. In a second mode, during fluid injection or withdrawal, and if desired, before and/or after injection or withdrawal, a plurality of electromagnetic measurements (images) are made. Based on the electromagnetic and hydraulic measurements, and a model which interrelates the measurements, determinations are made as to various characteristics of the formation, including effective permeabilities. Related methods for utilizing the tool and for treating the data in an integrated fashion are also set forth.

25 Claims, 10 Drawing Sheets

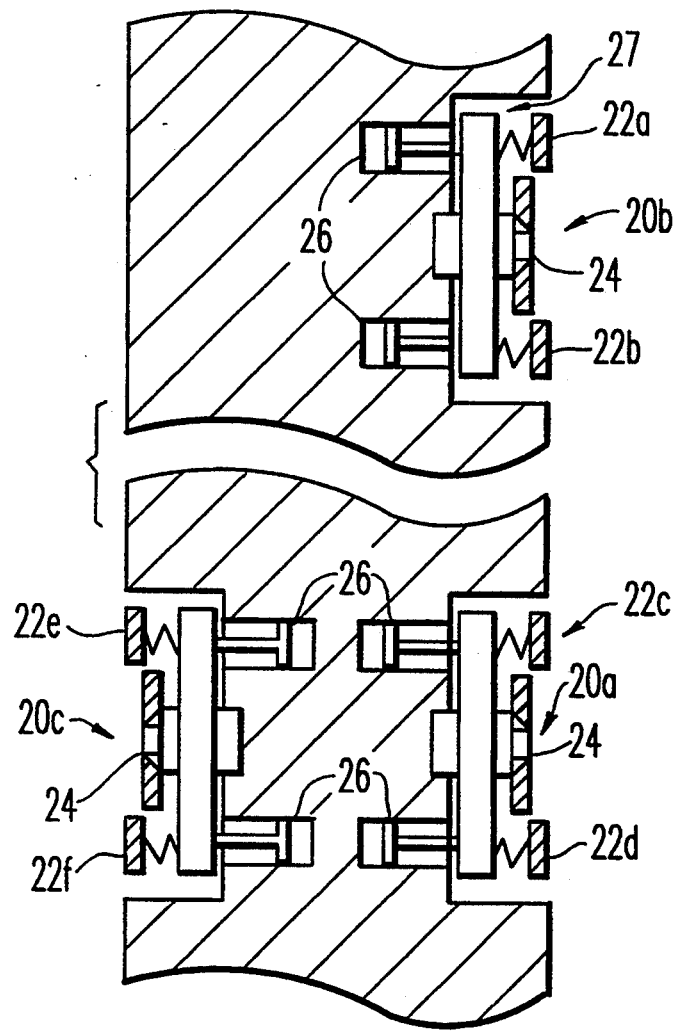
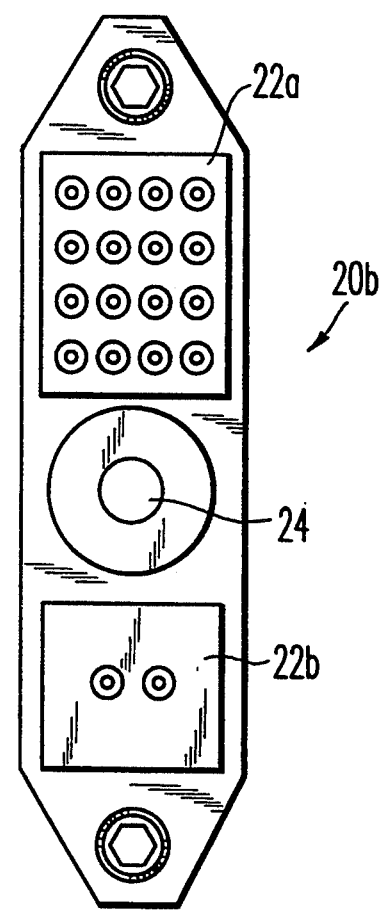
FIG. 2
FIG. 3

INTEGRATED PERMEABILITY MEASUREMENT AND RESISTIVITY IMAGING TOOL

This is a continuation-in-part of U.S. Ser. No. 07/761,213, filed Sep. 17, 1991, now U.S. Pat. No. 5,269,190, assigned to the assignee hereof, and hereby incorporated by reference herein in its entirety.

BACKGROUND

1. Field of the Invention

This invention relates broadly to apparatus and methods for investigating subsurface earth formations. More particularly this invention relates to borehole tools and methods for making permeability and other hydraulic property measurements of earth formations surrounding boreholes, wherein resistivity imaging techniques are utilized to locate the borehole tool, and/or to provide real-time data regarding the movement of fluid in the formation, and/or to help in interpretation of the obtained data from which hydraulic property determinations are made.

2. State of the Art

The determination of permeability and other hydraulic properties of formations surrounding boreholes is very useful in gauging the producibility of formations, and in obtaining an overall understanding of the structure of the formations. For the reservoir engineer, permeability is generally considered a fundamental reservoir property, the determination of which is at least equal in importance with the determination of porosity, fluid saturations, and formation pressure. When obtainable, cores of the formation provide important data concerning permeability. However, cores are difficult and expensive to obtain, and core analysis is time consuming and provides information about very small sample volumes. In addition, cores, when brought to the surface may not adequately represent downhole conditions. Thus, in situ determinations of permeability which can quickly provide determinations of permeabilities over larger portions of the formation are highly desirable.

Suggestions regarding in situ determination of permeability via the injection or withdrawal of fluid into or from the formation and the measurement of pressures resulting therefrom date back at least to U.S. Pat. No. 2,747,401 to Doll (1956). The primary technique presently used for in situ determination of permeability is the "drawdown" method where a probe of a formation testing tool is placed against the borehole wall, and the pressure inside the tool (e.g., at a chamber) is brought below the pressure of the formation, thereby inducing fluids to flow into the formation testing tool. By measuring pressures and/or fluid flow rates at and/or away from the probe, and processing those measurements, determinations regarding permeability are obtained. These determinations, however, have typically been subject to large errors. Among the reasons for error include the fact that liberation of gas during drawdown provides anomalous pressure and fluid flow rate readings, and the fact that the properties of the fluid being drawn into the borehole tool are not known accurately. Another source of error is the damage to the formation (i.e., pores can be clogged by migrating fines) which occurs when the fluid flow rate towards the probe is caused to be too large. See, e.g., Ramakrishnan et al., SPE 22689 (1991).

More recent patent disclosures of permeability testing tools include U.S. Pat. No. 4,742,459 to Lasseter, and U.S. Pat. No. 4,860,581 to Zimmerman et al. (both of which are assigned to the assignee hereof) which further develop the draw-down techniques. The Zimmerman et al. patent mentions that in the drawdown method, it is essential to limit the pressure reduction so as to prevent gas liberation. In order to prevent gas liberation, Zimmerman et al. propose a flow controller which regulates the rate of fluid flow into the tool.

Additional progress in in situ permeability measurement is represented by U.S. Ser. Nos. 07/761,213 and 07/761,214. In U.S. Ser. No. 07/761,213, now U.S. Pat. No. 5,269,180 the parent application hereof, borehole tools, procedures, and interpretation methods are disclosed which rely on the injection of both water and oil into the formation whereby endpoint effective permeability determinations can be made. In U.S. Ser. No. 07/761,214, now U.S. Pat. No. 5,247,830 methods are disclosed for making horizontal and vertical permeability measurements without the necessity for measuring flow rate into or out of the borehole tool. These inventions advance the art significantly. However, even with the improvements in permeability measurement techniques, the accuracy and scope of the information obtained is not to the level desired. In particular, in the formation fluid sampling tools, only a limited number of samples may be obtained which can be analyzed. Thus, the locations from which the samples are taken must be well chosen. Further, even if sampling of formation fluids is not desired, but measurements are taken via drawdown and/or injection and measuring, it will be appreciated that each procedure is time-consuming. Thus, it is desirable to gain large amounts of information from each procedure, and again location of the tool in the borehole is critical as is the quantity and quality of the data accumulated. For example, it might be desirable to take the vertical permeability in a portion of a formation which crosses a bed boundary or a fracture, or alternatively to avoid such a situation. To cross a bed boundary or fracture, accurate location of the tool is required such that one probe or sensor lies on one side of the bed boundary or fracture while the other probe or sensor lies on the other side of the bed boundary. Similar accuracy is required to avoid straddling a boundary or fracture if such is desired.

While bed boundary locations are determinable and thin beds are locatable via the use of other well established tools such as the FMS (Formation Micro Scanner—another mark of the assignee hereof, details of which are found in Ekstrom, M. P. et al., "Formation Imaging With Microelectrical Scanning Arrays"; *The Log Analyst;* Vol 28, No 3, May-June 1987), and other tools (both impedance and current injection tools), it will be appreciated that this information obtained from a previous investigation of the borehole must be correlated with the depth of the permeability tool being run in the borehole at the time for a proper setting of the permeability tool. The tool depth is typically determined by monitoring the cable from which the tool is hung. However, because of the stretching and twisting of the cable, among other things, the exact location and orientation of the tool vis-a-vis the formation is never as exact as desired.

SUMMARY OF THE INVENTION

It is therefore an object of the invention to provide a borehole tool having a permeability measurement means integrated with a electromagnetic measurement or imaging device whereby location of the permeability measurement tool relative to the formation can be precisely set.

It is another object of the invention to provide a borehole tool having probes which integrate fluid withdrawal/injection apparatus with an electromagnetic measurement apparatus, whereby electromagnetic measurements of the formation can be accomplished during injection of fluid into, or withdrawal of fluid from the formation.

It is a further object of the invention to provide a borehole tool having integrated electromagnetic measurement or imaging and permeability measurement features wherein the movement of different types of fluid in the formation caused by use of the permeability measurement tool can be mapped or imaged to provide water, oil, and gas flow information.

An additional object of the invention is to provide an integrated electromagnetic, fluid withdrawal/injection borehole tool useful in determining relative permeability.

Yet another object of the invention is to provide an integrated electromagnetic, fluid sampling/injection borehole tool where the pressure, flow, and permeability information is used in conjunction with the electromagnetic information to provide a three dimensional saturation/conductivity map or image of the formation.

In accord with the objects of the invention, a borehole tool is provided and broadly comprises at least one probing assembly having an electrode means for making an electromagnetic investigation of a formation and a fluid withdrawal and/or injection means for making a fluid flow investigation of the formation. The electrode means includes a plurality of electrodes on at least one laterally extending pad, with the electrodes making electrical contact with a segment of the borehole wall. The fluid withdrawal and/or injection means includes a hydraulic probe on the same, or preferably a second laterally extending pad which makes hydraulic contact with the formation and is substantially adjacent to the laterally extending electrode pads, with the second pad making hydraulic contact with the formation. In conjunction with the electrode means, circuitry is provided to permit the electrode means where appropriate, to either impress voltages on the formation or to inject current into the formation, and to make desired current and/or voltage measurements. In conjunction with the hydraulic probe, means for either injecting fluid into the formation or for withdrawing fluid from the formation are provided as well as means for making measurements regarding fluid flow properties of the formation adjacent the borehole wall.

In the preferred embodiment, the pads containing the electrodes and the hydraulic pad are all part of a single probe which has hydraulically setting pistons which urge the probe into contact with the borehole wall. In such an arrangement, the electrical pads are preferably spring biased to limit their setting force so as to prevent damage when the pistons force the probe into contact with the formation. Also, preferably the probe is only one of a plurality of similar probes, with the probes placed so as to provide both horizontal and vertical information; i.e., two of the probes are displaced vertically relative to each other, and two of the probes are displaced azimuthally relative to each other.

In conjunction with the borehole tool, a processor means is provided for taking data obtained by the electrodes and for generating determinations regarding the electromagnetic characteristics of the formation adjacent the electrodes. The generated information can take various forms such as a resistivity log or image. The processor means also can take data from other probes to provide larger scale determinations. Further, because the borehole tool includes means for measuring formation fluid pressure at each probe, the processor means can conduct permeability determinations in accord with prior art techniques. However, and more importantly, because the tool includes both electromagnetic and permeability probes, the data from those probes can be used together in a plurality of different manners to obtain desired information. For example, the resistivity information can be used to set the tool (and hence the hydraulic probe) at desired exact locations in the borehole. The setting of the tool can be conducted automatically if desired by comparing resistivity profiles with previously gained profiles from the same and/or different boreholes, or by providing other information to which a resistivity profile can be correlated. Additional resistivity information can then be obtained during drawdown or fluid injection to provide "images" of fluid flow through the formation; the changes in resistivity constituting a change in fluid which thereby permits tracking of different fluids and an understanding of the relative permeabilities. Of course, yet additional resistivity information can be obtained after drawdown or fluid injection during the period of time and/or after the formation returns to steady-state.

From the data obtained via the hydraulic probe(s) and the data obtained via the electromagnetic probes, various determinations regarding the properties of the formation can be made. These determinations, include, but are not limited to relative permeability, endpoint permeabilities, wettability, capillary pressure, etc.

Additional objects and advantages of the invention will become apparent to those skilled in the art upon reference to the detailed description taken in conjunction with the provided figures.

BRIEF DESCRIPTION OF THE DRAWINGS

FIG. 2 is a schematic diagram of the formation probe section of the integrated electromagnetic/permeability measurement tool of the invention.

FIG. 3 is a front view schematic diagram of an integrated probe of the invention.

DETAILED DESCRIPTION OF THE PREFERRED EMBODIMENTS

Figure 1:
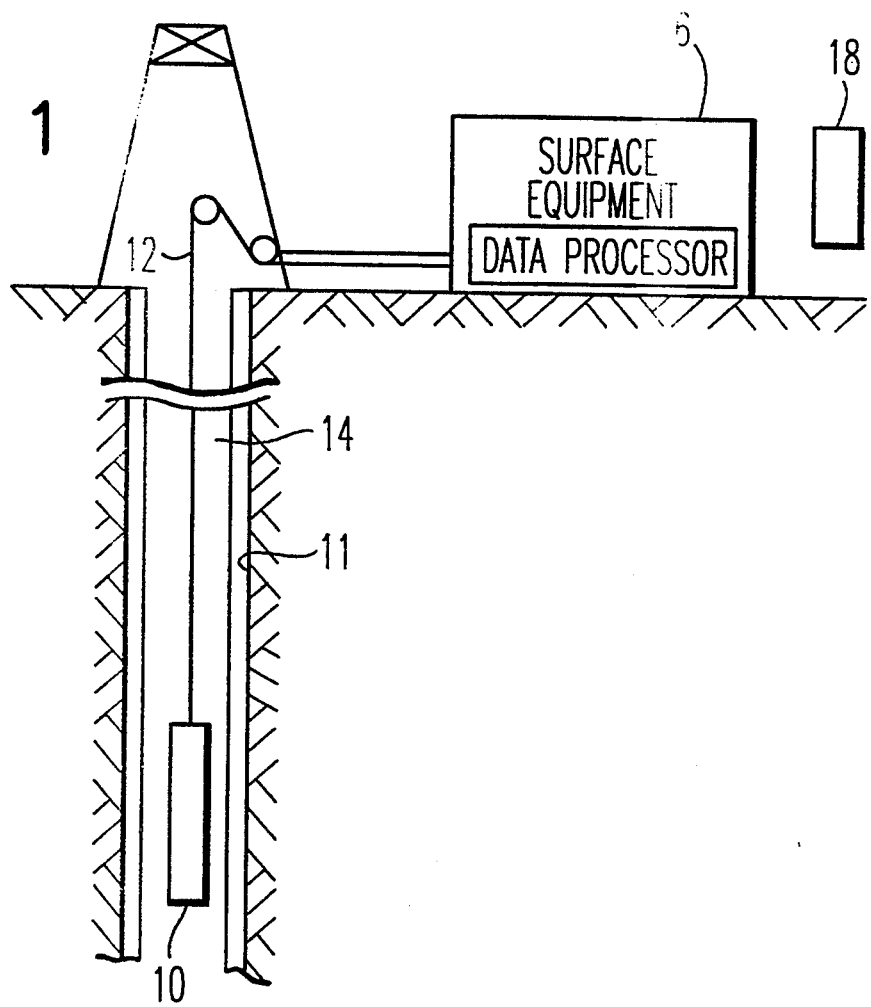
FIG. 1 is a schematic diagram of the system of the invention including the integrated electromagnetic/permeability measurement tool and an uphole signal processor.

Turning to FIG. 1, the basics of a borehole logging system are shown. A borehole tool or sonde 10 is shown suspended in a borehole 11 by a cable 12, although it could be located at the end of coil tubing. Cable 12, not only physically supports the borehole tool 10, but typically, signals are sent via the cable 12 from the borehole tool 10 to surface located equipment 16. The surface located equipment 16 may include a signal processor, a computer, dedicated circuitry, or the like which is well known in the art. Typically, the equipment/signal processor 16 takes the information sent uphole by the borehole 10, processes the information, and generates a suitable record such as a display log 18 or the like. Suitably, the information may also be displayed on a screen such as a CRT and recorded on a magnetic tape or the like.

Turning to FIGS. 2 and 3, schematic diagrams of the formation probe section of the integrated imaging-/permeability measurement tool 10 of the invention are seen. As shown in FIG. 2, the probe section 20 of the tool 10 preferably includes three probing assemblies 20a, 20b, and 20c, with probing assemblies 20a and 20b being vertically spaced, and probing assemblies 20a and 20c being spaced azimuthally around the borehole. As seen in FIGS. 2 and 3, each probing assembly 20 preferably includes at least one electrode 22 and one fluid sampling/injection apparatus 24. In fact, preferably, each probing assembly includes two sets of electrodes 22a and 22b (22c and 22d, 22e and 22f) with each set of electrodes including a plurality of electrodes.

In the preferred embodiment, each probing assembly 20 is brought into contact with the wall 11 of the borehole 14 by one or more hydraulically actuated pistons 26 which are used to force the probing assembly 20 outwardly. Because the fluid withdrawal/injection apparatus 24 requires that the probing assembly be in sealing contact with the borehole wall in order for effective measurements to be obtained, hydraulic actuated pistons 26 are capable of providing a large force on the probing assembly 20. However, because the electrodes 22 are typically more fragile, in order to avoid damage, the electrodes are preferably provided with springs 27 which spring bias the electrode pads and limit the setting force. Also, because one set of the electrodes (preferably 22a) are in contact with the borehole wall while the measurement tool 10 is moving, the springs bias the electrode pads to a position beyond the withdrawal/injection apparatus 24 which are used to contact the borehole wall only during a stationary procedure. Alternatively, electrodes 22a and others may be mounted on a separate hydraulic piston with spring bias so as to contact the borehole wall while moving in the borehole.

Figure 4:
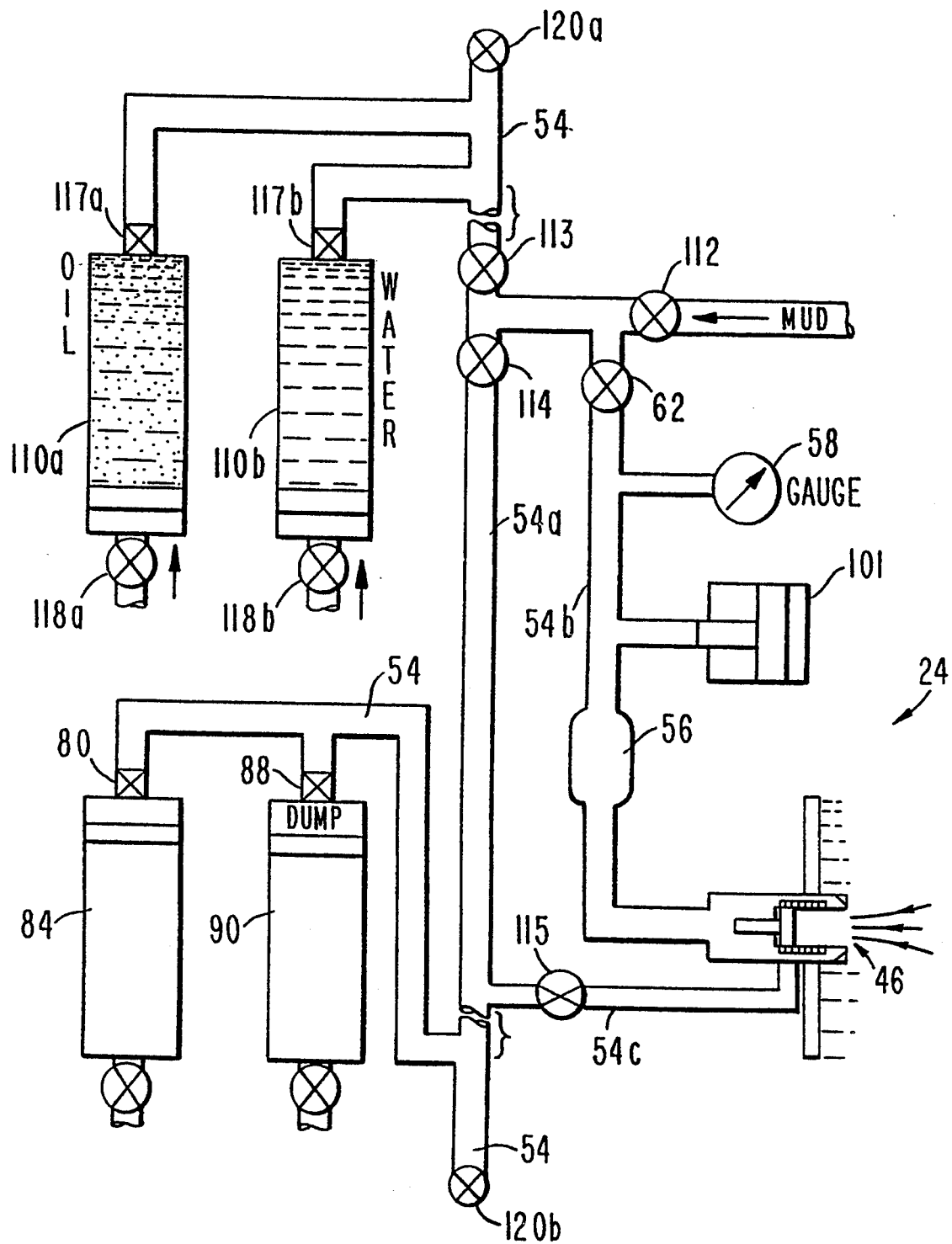
FIG. 4 is a schematic view of the preferred sampling/injection flow apparatus used to support the hydraulic aspect of the integrated probe of FIG. 2.

A better understanding of the preferred withdrawal/injection flow apparatus 24 is seen with reference to FIG. 4. However, before turning to FIG. 4, it should be appreciated that any probe which either samples fluid from the formation or injects fluid into the formation can be used in accord with the invention. Thus, among other fluid sampling or injecting apparatus, those suggested in U.S. Pat. No. 2,747,401 to Doll (1956), in U.S. Pat. No. 4,742,459 to Lasseter, and in U.S. Pat. No. 4,860,581 to Zimmerman et al. may be utilized.

As seen in FIG. 4, the components of the sampling-/injection flow apparatus 24 includes probe 46, flow line 54, resistivity cell 56, pressure gauge 58, isolation valve 62, formation sample chambers 84 and 90 and their associated valves 80 and 88, pretest expansion chamber 101, clean oil injection sample chamber 110a and associated valves 117a and 118a, the clean water injection sample chamber 110b and associated valves 117b and 118b, equalizing valve 112, bypass valves 113, 114, and 115, module valves 120a and 120b, and flow-line branches 54a, 54b, and 54c. Although not shown, additional clean fluid sample chambers can be provided, if desired.

In the preferred embodiment, the clean oil and clean water injection sample chambers 110a and 110b are respectively filled with clean oil and clean water samples of known viscosities, and are preferably located in the borehole tool above the isolation valve 62, pressure gauge 58, pretest chamber 101, and probe 46. Associated seal valves 117a and 117b, which may be driven hydraulically or electrically, are used to permit flow of oil and water out of the respective sample chambers and into flow line 54. The clean oil and clean water are used for flushing the flow line 54, and for injection into the formation.

Equalizing valve 112, which sits between a line open to borehole pressure and flow line 54, equalizes the differential pressure between the flow line 54 and the borehole while the tool is being run in the borehole. In the prior art, equalizing valve 112 is normally kept open during movement of the tool in the borehole. However, it is preferable to keep the equalizing valve 112 closed and the filter valve (which is part of the probe device 46) sealed in order to eliminate the flow of borehole mud into flow line 54. In order to keep equalizing valve 112 closed during borehole travel, a separate pressure compensator and valve mechanism must be provided. In fact, sample chambers 110a and 110b which are arranged as pistons can act as pressure compensators as long as they are provided with valves 118a and 118b which can be opened to the borehole mud. When valves 117a and 118a, or 117b and 118b are open, the pressure of the borehole acts on the respective chamber which in turn pressurizes flow line 54.

Isolation valve 62 isolates different sections 54a and 54b of the flow line 54 during different measurement sequences. It is also used to isolate lines 54a and 54b during the hereinafter described cleaning operation. The valve is preferably closed during pretest withdrawal or injection, thus isolating the rest of the tool flow line from the probe-pretest section.

Additional isolation valves 113, 114, and 115, which are also called bypass valves, are provided to isolate various sections of flow line 54. In particular, with isolation valves 62 and 115 closed, line 54b is completely isolated from line 54a. Such an arrangement may be desirable during a drawdown pretest. Such an arrangement is also provided in conjunction with open valves 113 and 114 when it is desirable to clean line 54a. On the other hand, where it is desirable to clean line 54b, isolation valves 112 and 114 can be closed with valves 113, 62, and 115 open. With this arrangement, fluid will flow through line 54 and valve 113, down through valve 62 and line 54b to probe 46 (with the filter valve preferably closed), and out through line 54c and valve 115. If valve 120b is closed and the valve 80 or 88 to one of sample or dump chambers 84 or 90 open, the fluid or material previously contained in line 54b and 54c will be dumped into the sample or dump chamber.

Because line 54c is preferably a small line which is coupled to the front of the probe 46 (which itself is of small diameter), when a sample is being taken from the formation for storage in chamber 84 or 90, bypass valve 115 and isolation valve 113 are closed, and isolation valves 62 and 114 are open. This permits a fluid sample which is taken from the formation to flow first through line 54b and then through line 54a. Alternatively, for fluid flow at low flow rates, bypass valve 115 can be opened and isolation valves 62 and 114 closed.

It will be appreciated by those skilled in the art that valve 113 effectively separates a domain of clean fluids from a domain of contaminated fluids. Similarly, while breaks in line 54 are intended to show separation of modules, valves 120a and 120b effectively isolate the beginning or end of the modules so as to force fluids in the desired directions.

Additional details of the sampling/injection flow apparatus 24 may be obtained by reference to the parent application hereto which was previously incorporated by reference herein.

Figure 5:
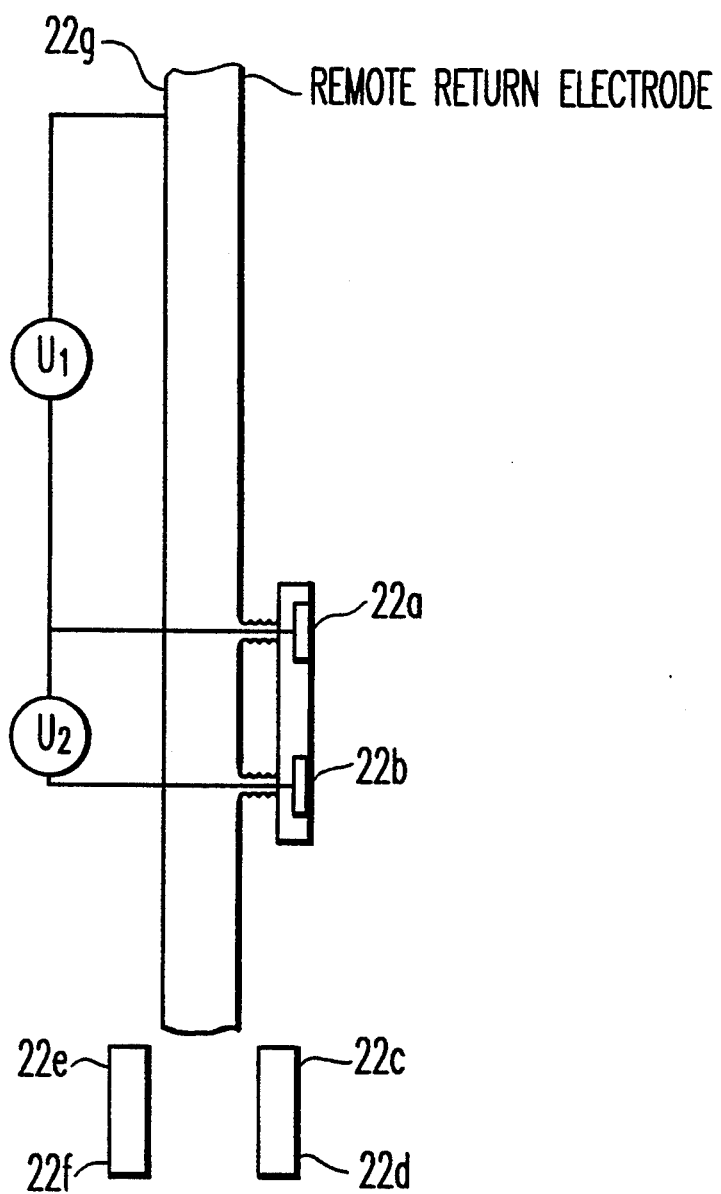
FIG. 5 is a schematic view of the preferred electromagnetic apparatus used to support the electromagnetic aspect of the integrated probe of FIG. 2.

FIG. 5 is a schematic view of the preferred electromagnetic apparatus used to support the electromagnetic aspects of the integrated probe of FIG. 2. Before turning to the details of FIG. 5, however, it should be appreciated that any of numerous electromagnetic apparatus can be used for formation imaging. For example, any of numerous induction or electrode devices may be used. Standard induction tools (see, e.g., Moran, J. and K. Kunz: "Basic Theory of Induction Logging and Application to Study of Two-Coil Sondes", *Geophysics* Vol. 27 (1962)) use groups of antennas which are coaxial with the wellbore and provide axisymmetric information about formation conductivity. An alternative induction logging tool employs small groups of miniature induction coils mounted on pads (see e.g., U.S. Pat. No. 4,712,070 to Clark and Chew) and is more suitable for measuring a nonaxisymmetric distribution of conductivity.

As with induction logging, there are several different techniques and tools known in the art utilizing electrodes. These measuring systems inject currents into, or impress voltage on the formation via electrodes typically applied against the surface of the formation to be investigated, and measure the resulting induced voltages or currents on the same or additional electrodes. One group of such tools include passively focused electrodes, where a conducting pad with an array of the electrodes is articulated to the borehole surface with the electrodes isolated from each other and held at a constant potential relative to a distantly located return electrode. Current flows into the formation from the array of electrodes, and a sampling of the electrode currents across the pad is used to determine local resistivity variations in the formation in front of the pad. Shallow imaging of the formation at the borehole wall is thereby obtained. At the same time, data obtained at a return electrode distantly spaced is used to give average resistivity information ever a larger segment of the formation. A more detailed description of one such passively focused tool (the FMS tool—a trademark of Schlumberger Technology Corporation) is found in Ekstrom, M. P. et al., "Formation Imaging With Microelectrical Scanning Arrays"; *The Log Analyst;* Vol. 28, No. 3, May-June 1987).

Another group of electrode tools use an active focusing scheme with one or more guard electrodes to control the volume of the formation being investigated. One example of this type of tool is the MSFL or MicroSpherically Focused Log tool (trademarks of Schlumberger Technology Corporation) which uses a set of concentric rectangular electrodes to probe a volume of the formation. Details of the MSFL are set forth in, e.g., Ellis, Darwin: *Well Logging for Earth Scientists,* Chapter 7, Elsevier, New York (1987), where a pad with five electrodes is provided, including three voltage measurement electrodes and two current emittting electrodes. One of the current emitting electrodes provides a bucking current which forces the current path of the other current emitting electrode to be forced into the formation. An alternative technology to the MSFL uses active focusing in the azimuthal direction and passive focusing in the vertical direction. This hybrid focusing scheme has been employed to provide a quantitative map of conductivity several inches into the formation in front of the pad. Details of the hybrid focusing scheme may be obtained with reference to application number EPO 89 02158.

Yet another alternative tool is a high resolution electromagnetic probing tool known as the Electromagnetic Propagation Tool or EPT (a trademark of Schlumberger Technology Corporation). The EPT has a sensor which excites a very high frequency propagating wave, and from measurements of the propagation velocity and rate of attenuation, determines the formation conductivity and dielectric constant with a spatial resolution on the order of inches.

Turning now to FIG. 5, a schematic of the preferred electromagnetic apparatus of the integrated probe assembly is seen. Two sets of electrodes 22a, 22b are preferably provided on each probe assembly and the electrodes are preferably uniform potential type electrodes. Preferably, each set of electrodes 22a, 22b includes a plurality of axially and azimuthally spaced electrodes (e.g., sixteen electrodes for pad 22a and four electrodes for pads 22b, 22c . . . ), although a single electrode could be utilized in sets 22b, 22c . . . . While the electrodes type can be chosen from any of the above described types of electromagnetic tools, in the preferred embodiment, a passive focusing arrangement is used similar to that described in Ekstrom, M. P. et al., "Formation Imaging With Microelectrical Scanning Arrays"; *The Log Analyst;* Vol. 28, No. 3, May-June 1987). In particular, each electrode is surrounded by a thin ring of insulating material electrically separating it from the surrounding metallic pad material. All button electrodes and the surrounding pad material for a single pad are held at the same voltage potential through the use of isolation transformers or operational amplifier input circuitry, with each pad held at an AC electrical potential whose amplitude and frequency may be fixed. For a sufficiently large pad area, currents emanating from the points not near the pad boundary tend to travel nearly perpendicular to the pad face; i.e., into the formation as opposed to immediate short-circuiting through the borehole mud or mudcake. In the preferred embodiment, the electrode arrangement is surrounded by a large metallic area to ensure that much of the current flows through the formation. Currents measured with button electrodes situated on the interior part of the pad correspond to currents that have travelled through the interior of the formation.

As shown in FIG. 5, a low frequency voltage U1 (e.g., 1 kHz) may be impressed between the top electrical pad 22a and a remote return electrode 22g. This configuration corresponds to the FMS logging mode (see Ekstrom, et al.), where the distribution of current density across the face of pad 22a is directly related to the spatial distribution of shallow conductivity in front of the pad. Two dimensional imaging samples of this current density may be used in a first imaging mode to image shallow formation conductivity for purposes of probe positioning. In a second imaging mode which takes place during fluid sampling, a voltage U2 may be impressed between the lower electrical pad 22b and the top electrical pad 22a. This causes currents to flow between pads 22a and 22b through the formation directly in front of the sampling probe 24. Each of the electrodes and associated electronics is preferably capable of measuring a plurality of voltages at different frequencies as necessary. Details of the electrode electronics is known to those skilled in the art, and additional reference to U.S. Pat. Nos. 3,772,589 to Scholberg, 4,251,773 to Cailliau et al., 4,594,552 to Grimaldi et al., and 5,036,283 to Trouiller et al. may be helpful.

With the tool of the invention having its resistivity and permeability measurement capabilities physically adjacent each other, tool 10 can be used in either of two primary manners: using the electromagnetic (resistivity) measurement and/or imaging capabilities to find exact locations of interest at which to set the tool and taking permeability measurements thereat; and using the electromagnetic measurement and/or imaging capabilities to find exact locations of interest at which to set the tool, and using electromagnetic measurement and/or imaging during the permeability experiments to further an understanding of the parameters of the formation.

Figure 6:
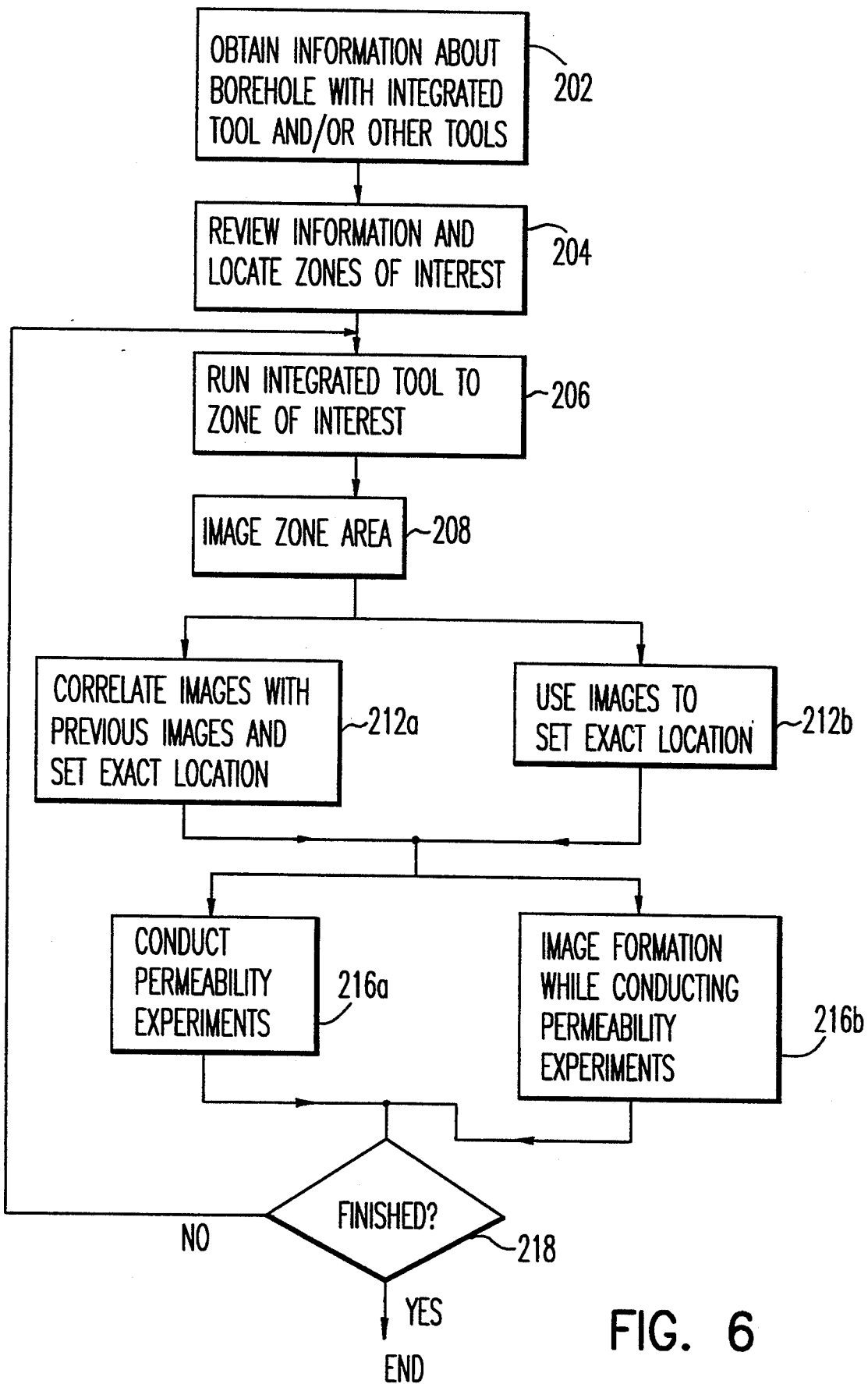
FIG. 6 is a flow chart of preferred modes of operation of the integrated electromagnetic/permeability measurement tool of the invention.
Figure 7A:
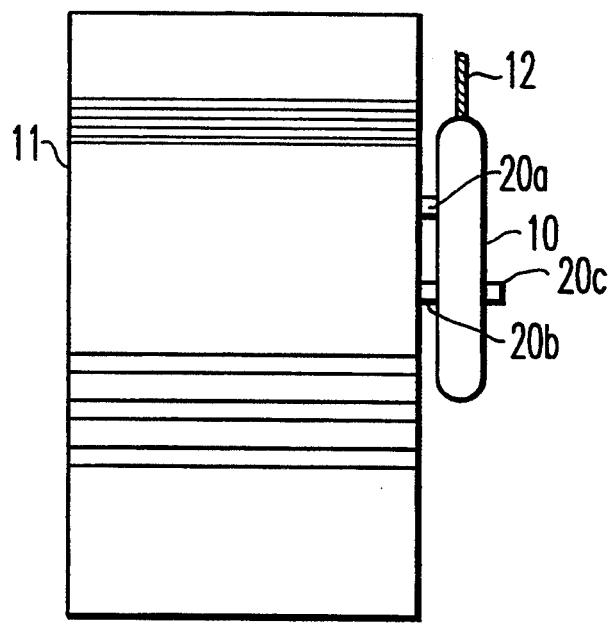
FIGS. 7a and 7b show the preferred tool of the invention with its hydraulic probes located at a homogeneous zone and straddling a thin bed location of a formation respectively.
Figure 7B:
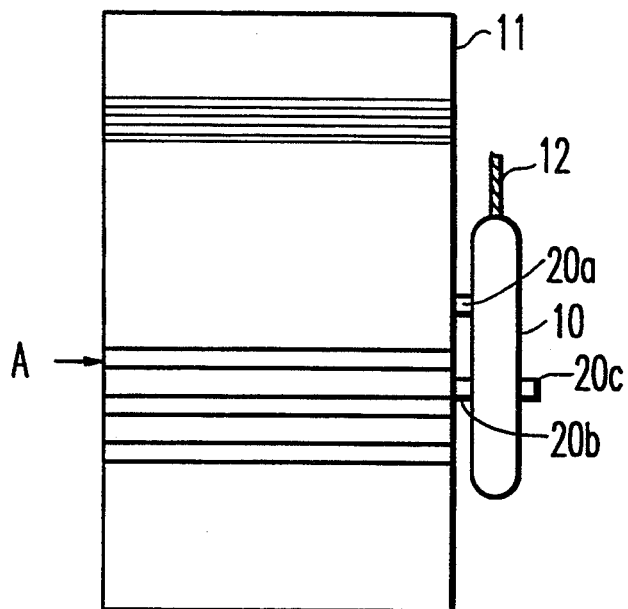

Preferred manners of utilizing the capabilities of the tool for the purposes of setting the tool at desired locations are seen in FIG. 6. In particular, at 202, a pass of the borehole with the tool 10 of the invention or some other tool is accomplished first. Review of the generated logs by the operator, consultant, or an expert computer system, at 204 permits depths (zones) of interest to be located. In identifying zones of interest, review of one or more of the following is desirable: interpretable zones; zones requiring special care in tool placement; fractured zones; thinly laminated zones; massive reservoir rock; structural dip; sedimentary dip/structure; permeability barriers, etc. It will be appreciated that the generated logs which are reviewed may be resistivity images such as are obtained by induction logging or electrode tools as discussed above, or can be plots or other images such as might be generated by, inter alia, nuclear (neutron, gamma-ray, etc.) type tools or acoustic type tools. Regardless, once the depths of interest are located, the tool 10 of the invention is run at 206 to approximately a first depth of interest. Where the first log or image was made by a tool having similar capabilities to tool 10, the exact positioning of tool 10 to the first depth of interest may be made by having tool 10 provide resistivity images at 208 and correlating these images at 212a with the previously obtained images. Alternatively, and regardless of the type and detail of the information obtained previously, upon reaching the approximate location of depth of interest, the resistivity images obtained at 208 are used by the operator at 212b to locate the tool 10 at an exact location of interest. The exact location of interest may be in a relatively homogeneous zone as suggested by FIG. 7a, or a thin bed zone as suggested by FIG. 7b. Of course, other types of zones may also be of interest.

In accord with one embodiment of the invention, once the tool 10 is set at the desired location, permeability experiments including fluid sampling and/or fluid injection are carried out at step 216a according to any of many techniques to provide permeability determinations. Thus, preferably techniques disclosed in one or both of Ser. Nos. 07/761,213 and 07/761,214 are utilized. However, in accord with another embodiment of the invention which is described in more detail hereinafter with reference to FIG. 8b, electromagnetic measurements of the formation are carried out during the fluid withdrawal and/or fluid injection at 216b, and the changing electromagnetic measurements are utilized in conjunction with the pressure and flow rate data obtained during fluid withdrawal and/or fluid injection to provide information (e.g., permeability determinations) regarding the formation. Upon termination of the fluid withdrawal and/or injection and when appropriate, upon the completion of electromagnetic measurement and/or imaging, a determination is made at 218 whether another zone of interest is to be investigated. If so, the tool is moved at step 206 to the next zone of interest, and steps 208, 212 (a or b), and 216a and 216b are repeated. The loop is typically continued until all zones of interest are investigated.

While a first pass through the borehole to locate zones of interest may be preferable as discussed above, it will be appreciated by those skilled in the art that no such first pass is required. Instead, the information required for locating zones of interest for permeability measurements may be obtained as the tool is being lowered into the borehole, and the measurements may be made as the tool is being moved up the borehole. As another alternative, as the tool is being lowered and/or as the tool is being lifted out of the borehole, determinations based on the imaging information can be made on the spot based on the desirability of obtaining a permeability measurement at that depth.

Before turning to the preferred manner of processing the information gained during operation of the integrated imaging/permeability measurement tool of the invention, a discussion of the physics and mathematics underlying the invention is helpful. In particular, the preferred embodiment of the measurement tool of the invention probes the interior of the formation volume V by applying equipotential metallic pads, each at a different voltage, to the surface δV of the volume, measuring the resulting currents flowing into the metallic electrodes contained on the pads, and from this information, inferring, with the help of an associated fluid dynamic model, the position and/or movement of electrically conducting (brine) and insulating (oil) fluids during the sampling procedure. Essentially, an approximation of the spatial distribution of conductivity in the formation is reconstructed. Mathematically, if u is the electric potential, and $\sigma$ is the conductivity, then u satisfies:

$$\nabla \cdot \sigma(\underline{r}) \nabla u(\underline{r}) = 0 \text{ for } \underline{r} \text{ in } V \quad (1)$$

$$-\sigma(\underline{r}) \partial u(\underline{r})/\partial \tau = j(\underline{r}) \text{ for } \underline{r} \text{ on } \delta V \quad (2a)$$

where $\tau$ denotes the outward unit normal to the formation, j denotes the current density at the surface of the formation, and $\underline{r}$ denotes a position vector. Because current densities are not specified, but rather voltages applied to pads are specified and currents are measured at electrodes, the current density may be integrated over the electrode surface area so that equation (2a) becomes $$\sigma(\underline{r}) \partial u(\underline{r})/\partial \tau = I_1/A_1, \text{ for } \underline{r} \epsilon e_l \quad (2b)$$

at the l'th electrode. Here, L is the number of electrodes, $e_l$ is the l'th electrode, $I_l$ is the current measured at the l'th electrode, and $A_l$ is the area of the l'th electrode. The impressed voltages on the pads (U) are chosen so that the sum of voltages on the pads is zero.

The electrical conductivity $\sigma$ of the formation depends on the spatial position r (radius) in the formation volume as well as time t. Hence, the conductivity is denoted as $\sigma(r,t)$. Because the formation generally contains a two-phase fluid distribution, and fluids are moving with time during injection and/or fluid withdrawal, the conductivity will change over time.

In the preferred measurement, the equipotential pads are each held at a different potential (U denoting the impressed voltage pattern), causing currents to flow between each of the pad pairs. These currents are sensed using spatially distributed arrays of electrodes on the face of each pad. If $I_k(t_j)$ denotes the current measured on the k'th electrode at the j'th time instant, and I denotes the collection of all measured time samples of electrode currents, then equation (1) may be specialized to the preferred pad and electrode geometry to represent a general mathematical model, denoted E, which for a given conductivity $\sigma(r,t)$ relates the impressed voltages $\underline{U}$ to the measured currents $\underline{I}$. In particular, $$\underline{I} = E[\sigma(r,t), \underline{U}] \quad (3)$$

From the limited number of electrode current measurements (I) made using the preferred electrical measurements, the complete time-varying conductivity distribution $\sigma(r,t)$ cannot easily be inferred. Only a crude approximation may be possible in which $\sigma(r,t)$ is partitioned into a few regions of uniform conductivity. Alternatively, additional information may be used to interpret the results of these electrical measurements to get $\sigma(r,t)$.

In accord with the preferred embodiment of the invention, such additional information is obtained from the characteristics (e.g., permeability, relative permeability, etc.) of the dynamic fluid flow (which characteristics may be obtained via processing of information obtained by the hydraulic probe of the invention or assumptions which may be based on previous knowledge), since these characteristics restrict the range of possible conductivity patterns $\sigma(\underline{r},t)$; i.e., the evolution of conductivity distribution during fluid sampling is constrained by petrophysical and fluid flow processes. In other words, the petrophysical and fluid flow constraints of the system can be used to provide initial resistivity distribution information, and the equations governing fluid flow and petrophysical processes can be used to provide additional constraining information regarding conductivity changes. Conversely, as will be described hereinafter, the resistivity information can at the same time be used to provide a more robust determination of various of the fluid flow characteristics of the formation.

The petrophysical and fluid flow processes can be described as follows. For simplicity, dispersion and capillary pressure are ignored, and it is assumed that the formation is uniform and homogeneous in the interval of interest. The fluids in a region close to the tool are also assumed to be incompressible, and gravity is ignored in view of the short time scales involved during sampling during which buoyancy segregation is likely to be extremely small. Based on the above assumptions, the governing equations are:

$$\nabla \cdot \underline{v} = 0 \quad (4)$$

where $\underline{v}$ is the sum of the filter velocities of oil and water, and where equation (4) describes conservation of mass, $$\phi \partial S/\partial t + \underline{v} \nabla f_w = 0 \quad (5)$$

where $\phi$ is the porosity, $f_w$ is the fractional flow of water, S is the water saturation, and where equation (5) describes conservation of aqueous phase components, and $$\phi S \partial \Gamma/\partial t + \underline{v} f_w \nabla \Gamma = 0 \quad (6)$$

where $\Gamma$ is a measure of the salt concentration which is equal to one for a saturated salt solution and equal to zero for pure water, and where equation (6) describes conservation of salt. It is assumed that negligible volume change occurs by the mixing of native water and the mud filtrate.

In addition to equations (4) through (6), the formation is characterized by the relationship between fluid velocity and pressure p by an extended form of Darcy's equations:

$$\underline{v} = -B\Omega \cdot \nabla p \quad (7)$$

where B is the permeability tensor, and $\Omega$ is the sum of oil and water mobilities. By assuming that the pressures of the phases (water and oil) are equal, and that the principal directions for the permeability tensor are known, and further that the well is perpendicular to the bedding layer, equation (7) presents two unknowns for the permeability tensor: the radial direction permeability $\beta_r$, and the vertical direction permeability $\beta_z$. However, a good estimate for these unknowns may be obtained from multiprobe interpretation of pressure data obtained from tests in a couple of different manners (see, Goode and Thambynayagam, "Analytic Models for a Multiprobe Permeability Tool: The Modular Formation Dynamics Tester" *Annual Technical Conference of SPE*, New Orleans, La. (1990), and the parent applications hereto). Additional unknowns are $f_w$ and $\Omega$ which are expressed in terms of relative permeabilities. Relative permeabilities are hysteretic functions of saturations and as set forth in Ramakrishnan and Wasan, "Effect of Capillary Number on the Relative Permeability Function for Two-Phase Flow in Porous Media"; *Powder Technology* 48, pp 99–124 (1986), can be described in terms of a few parameters such as connate water saturation ($S_{wc}$), residual water saturation ($S_{wr}$), maximum residual oil saturation ($S_{orm}$), and pore size distribution index ($\alpha$).

The relationship between the petrophysical aspects of the formation and the formation conductivity may be expressed as:

$$\sigma = \sigma(\phi, \Gamma(\underline{r},t), S(\underline{r},t)) \qquad (8)$$

where $\Gamma(\underline{r},t)$ and $S(\underline{r},t)$ are solutions to the differential equations (4)-(7) above, and are subject to initial and boundary conditions. Initial conditions are typically determined by the invasion process which can take place over a long period of time (e.g., several days). Thus, when specifying initial conditions, account may be taken of dispersion, capillary pressure and gravity which may influence the saturation and conductivity profiles. For simplicity, equations (4)-(8) may also be used for setting up the initial conditions, particularly in the radial direction. In both cases, the filtrate loss per unit depth Q will enter as an unknown.

For boundary conditions, many different models can be utilized. Top and bottom boundaries can be included, or fictitious boundaries sufficiently far away from the probe which would not affect the determinations can be introduced. If real boundaries are known (e.g., via formation images), these real boundaries can be included. Since in a layered system, steady state flow is never reached if the formation is of infinite lateral extent, the steady state nature of equations (4)-(7) may be coupled to compressible flow in an "outer" region. Other boundary conditions are more similar over different models, including the assumption of no flow through the wellbore, and no flow through top and bottom boundaries. Over the area of a given probe, the pressure is uniform, and the measured pressure is used as the boundary condition.

It will be appreciated that in solving for unknowns, the more relevant information that is available, the more robust the solution. Thus, flow rate information is preferably obtained either by sensing the rate of change of fluid volume in the sample chamber, or via use of a Venturi or other flow rate probes. Similarly, fractional oil and water flow rates may be obtained via use of an optical analyzer such as is disclosed in U.S. Pat. No. 4,994,671 to Tarvin and Safinya.

Figure 8A:
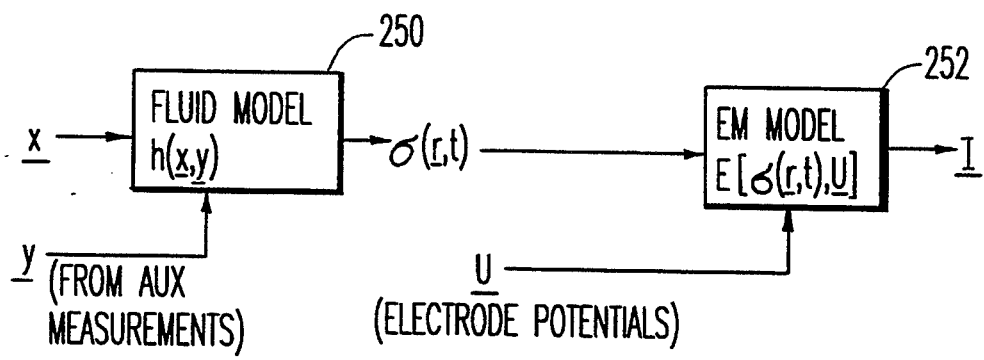
FIG. 8a is a flow chart of a forward problem which relates information gained from the resistivity and hydraulic probes.

The formation properties used to describe the petrophysical aspects of the formation may be divided into those aspects which may be measured through auxiliary measurements such as wireline logs, nearby well core measurements, uphole fluid samples, etc., and those aspects which are inferred only through the formation test measurements (i.e., the unknowns). Among the common auxiliary measurements would be porosity, the Archie exponents in the resistivity-saturation relationship (n, m), oil and water viscosities ($\mu_o, \mu_w$), and the native water and mud filtrate conductivities ($\sigma_c, \sigma_m$), while among the common variables which are unknown but for which determinations are desired are connate water saturation ($S_{wc}$), residual water saturation ($S_{wr}$), maximum residual oil saturation ($S_{wo}$), pore size distribution index ($\alpha$), and filtrate loss per unit depth (Q). If the auxiliary measurement variables are denoted $\underline{y}$, and the unknowns are denoted $\underline{x}$, the mapping or relation between the input formation variables and the resulting spatial distribution of formation conductivity can be denoted by h according to $$\sigma(\underline{r},t) = h(\underline{x},\underline{y}) \qquad (9)$$

as indicated in FIG. 8a at 250.

As shown in FIG. 8a, the dynamic fluid model h and the previously discussed electromagnetic model E are preferably combined. As indicated at 252, the electrode currents I depend upon the pad/electrode voltages U and the conductivity distribution $\sigma(\underline{r},t)$, which in turn depends on the formation properties $\underline{x}$, and $\underline{y}$. Thus, based on the known pad/electrode voltages U, the measured electrode currents I, and the known formation properties $\underline{y}$, it is desirable to provide a determination of the unknown formation properties $\underline{x}$.

Figure 8B:
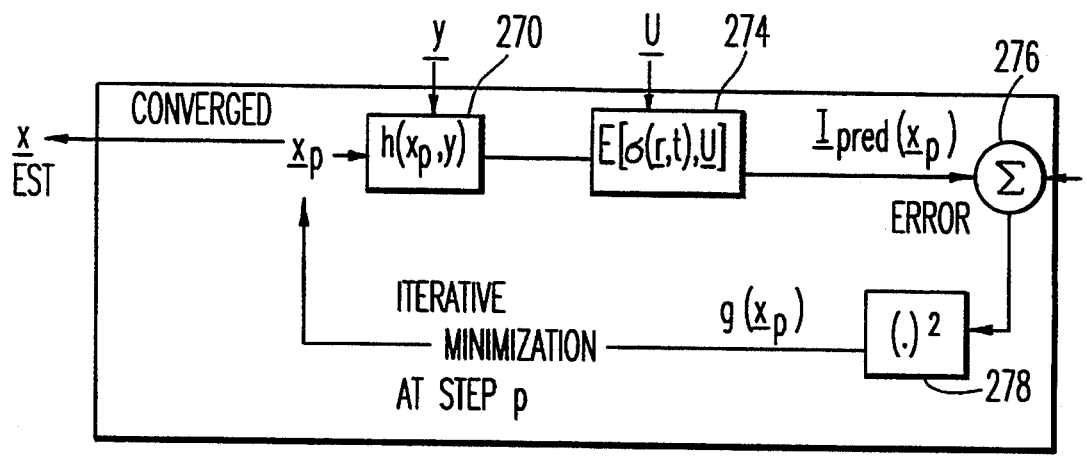
FIG. 8b is a flow chart of the preferred manner for solving for the unknown electromagnetic and hydraulic properties of the formation.

In order to solve for the unknown formation properties (i.e., the inverse problem), an iterative optimization is utilized. In particular, as seen in FIG. 8b, using the dynamic fluid model h and the electromagnetic model E, first guess estimates of $\underline{x}$ (denoted $\underline{x}_0$) and values $\underline{y}$ are input into the fluid model at step 270, to provide a value for the impedances a $\sigma(\underline{r},t)$. The impedance values and the known pad/electrode voltages U are then input into the electromagnetic model E at step 274 to provide predicted values $I_{pred}$. The predicted values $I_{pred}$ are then compared at 276 to the actual measured values I to provide an error signal. The error signal is squared at step 278 and used in a suitable iterative algorithm such as Newton's method or the Conjugate Gradient Method (see, Luenberger, D., *Introduction to Linear and Nonlinear Programming*, Addison-Wesley, Reading Me. (1973)), perhaps with regularization (see, Menke, W., *Geophysical Data Analysis: Discrete Inverse Theory*, Academic Press, San Diego, Calif. (1989)) to obtain a refined estimate of $\underline{x}$. Newton's method, for example, leads to an iteration of the form $$\underline{x}_{p+1} = \underline{x}_p - [G(\underline{x}_p)]^{-1} \nabla g(\underline{x}_p)' \qquad (10)$$

where the subscript p refers to the p'th iteration, and where $\nabla g(\underline{x})$ is the gradient of g, and $G(\underline{x})$ is Hessian matrix of second derivatives of g, and the prime (') denotes a matrix transpose. As suggested by FIG. 8b, the iterative minimization continues until the minimization converges to an estimate of $\underline{x}$.

Figure 8C:
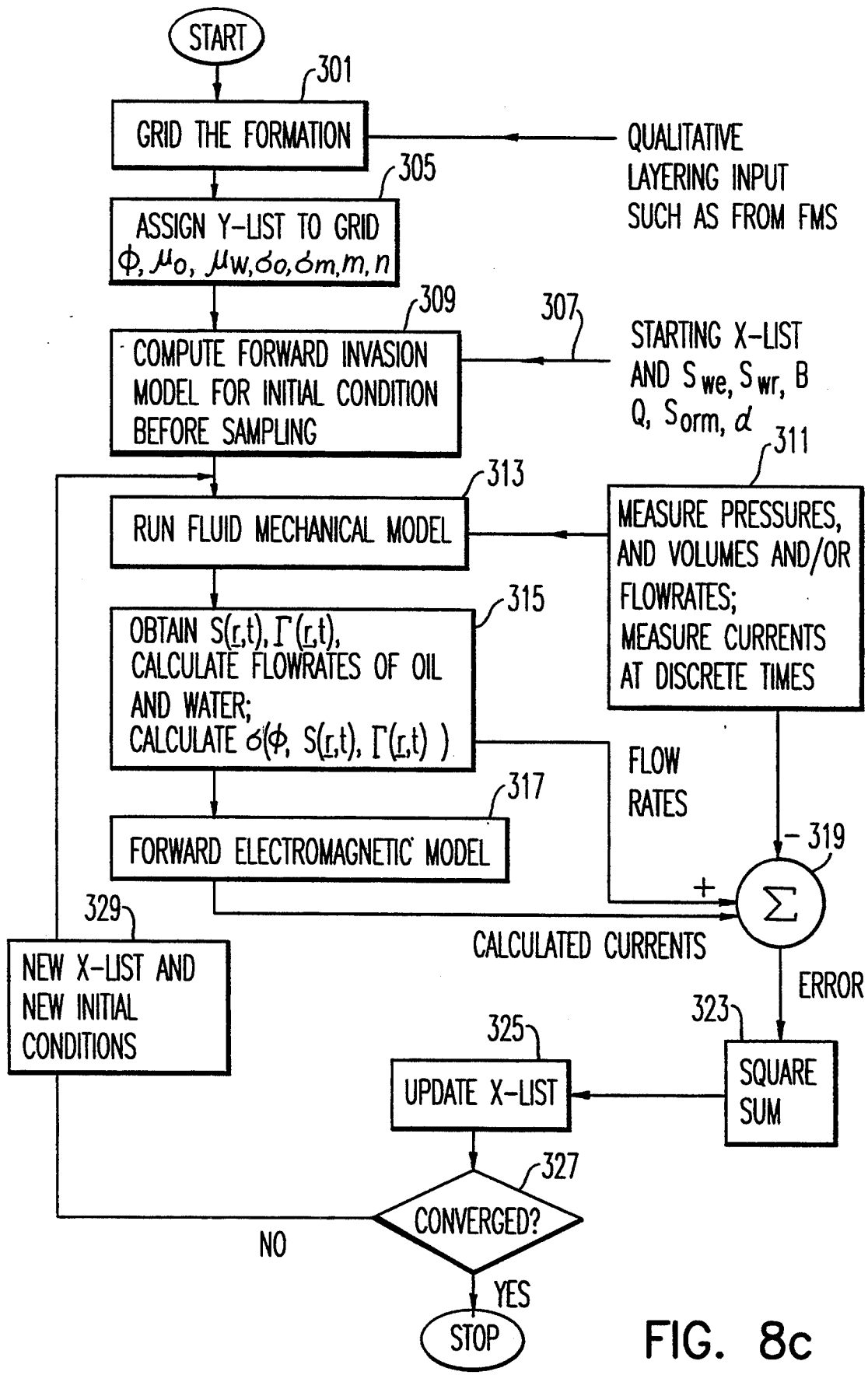
FIG. 8c is a more detailed flow chart of the method of the invention.

Using the above teachings, a more detailed flow chart of the method of the invention is seen with reference to FIG. 8c. In particular, at step 301, the formation is divided into a grid utilizing available layering information such as might have been obtained from the previous running of an FMS tool. At step 305, the "known" parameter values (the "y" list) are assigned to the grid. The known parameter values, which are typically available through other logs, correlation, or prior experience, include porosity ($\phi$), the viscosity of oil ($\nu_o$), the viscosity of water ($\mu_w$), the native water conductivity ($\sigma_w$), mud filtrate conductivity ($\sigma_m$), and the Archie exponents m and n. In addition, qualitative information determined by other tools such as gamma ray tools, sonic tools, etc., such as the identification of bed boundaries can be utilized in assigning the y-list values to the grid.

At step 307, starting guesses for the unknowns ("x-list") are provided. Included on the x-list might be $S_{wc}$, $S_{wr}$, $S_{orm}$, $\alpha$, Q, and the permeability tensor B as described above. A guess for B may be obtained from the interpretation of measurements according to co-owned Ser. No. 07/761,214 to Peter Goode, and can include a damaged skin region. The skin region represents a small zone adjacent to the sink probe where progressive permeability reduction might occur due to fines migration. Thus, a time dependent permeability is assigned to a small zone adjacent to the hydraulic probe in the numerical model. With the grid as set forth at step 305, and the values for the x-list supplied at step 307, the initial conditions for a forward invasion model such as described in e.g., Phelps et al., "The Analysis of the Invaded Zone Characteristics and Their Influence on Wireline Log and Well Test Interpretation", *SPE* 13287; 59th Ann. Tech. Conf. & Exhibition, Houston (1984) are computed at step 309 before hydraulic measurements are made.

At step 311, hydraulic and electromagnetic measurements are made using the hydraulic and electromagnetic probes of the preferred tool. Among the hydraulic measurements made include the cumulative amount of fluid withdrawn into the sample chamber or injected into the formation, and the pressure at the sink (source), and horizontal and vertical probes. Preferably, independent measures of the oil and water flow rates are made, thereby also providing a total flow rate. Using the obtained measurements of step 311 and the initial conditions for the forward invasion model of step 309, a fluid mechanical model is run at step 313. The fluid mechanical model may be a finite element or a finite difference calculation of the differential equations (4)-(8) set forth above. As a result, at step 315, $S(r,t)$ and $\Gamma(r,t)$ are obtained, and flowrates of oil and water into the tool are calculated from the numerical calculations. In addition, the conductivity distribution $\sigma(\phi,\Gamma(r,t), S(r,t))$ is calculated at step 315. With this information, at step 317, the forward electromagnetic model $E[\sigma(r,t),U]$ is run as discussed above with reference to FIG. 8a. The results of the hydraulic/electromagnetic model are then compared at 319 with the hydraulic/electromagnetic measurements made at step 311 in accord with the discussion above with reference to FIG. 8b. The electromagnetic measurements include the current at each of the buttons located on the pads as well as the voltages $\underline{U}$ applied to each of the pads. The voltages applied are preferably measured due to the possibility of loss through cables, and other extraneous reasons.

Based on the difference between the expected electromagnetic values and the determined values, a squared error is taken at step 323, and the x-list is updated for new values at step 325. At 327, a determination is made as to whether a convergence has been reached. If not, the forward invasion model is computed for the new x-list at step 329, and steps 313 through 327 are repeated until a solution is found; i.e., satisfactory convergence is obtained.

According to another aspect of the invention, instead of impressing voltages and measuring currents (i.e., using passively focused electrodes), the electrodes used in conjunction with FIG. 5 are current injection electrodes (such as actively focussed electrodes), which are capable of injecting current into the formation at desired frequencies and are also capable of measuring resulting voltages as a function of frequency. The preferred electrodes for this arrangement are described hereinafter with reference to FIG. 11. With this arrangement, the currents applied through the electrodes are specified and the voltages are measured. While much of the above-described physics and mathematics is relevant to this situation, some of the equations must be changed. For example, equation (2b) is now written:

$$\sigma(\underline{r})\delta u(\underline{r})/\delta\tau = I_l/A_l, \text{ for } \underline{r} \in e_l \quad (11)$$

$$0, \text{ for } r \bigcup_{l=1}^{L} e_l$$

where $I_l$ is the current injected into the l'th electrode, and the current density is defined as zero in the gaps between electrodes.

With the voltage being measured, the imaging of the formation is done by solving for conductivity $\sigma(\underline{r},t)$ at any point $\underline{r}$ within the formation volume V at time t. Where the conductivity is not changing, i.e., the problem is static, it is clear that problem reduces to solving the conductivity of $\sigma(\underline{r})$. However, where there is a formation with two-phase fluid distribution and fluid flow, as will be the case upon fluid injection and/or fluid sampling, the conductivity will change over time.

In solving for the conductivity at points r over time, the problem may be discretized in time to obtain a series of J snapshots of the conductivity distribution at specified times $t_j$, for $j=1, \ldots, J$. The spatial conductivity distribution at the $j^{th}$ time instant is denoted according to $$\sigma^{(j)}(\underline{r}) = \sigma(\underline{r},t_j) \quad (12)$$

During the electrical imaging measurement process, an array of L spatially distributed conducting electrodes is applied to the borehole wall. For the $j^{th}$ time snapshot, K different electrical current patterns are injected into the electrode array. The $k^{th}$ current pattern applied to the L electrodes at time $t^j$ is denoted $\underline{i}^{(j)}{}_k = (i^{(j)}{}_{k1}, i^{(j)}{}_{k2}, \ldots, i^{(j)}{}_{kL})$, and the collection of all K current patterns injected at time $t_j$ is denoted as $\underline{I}^{(j)} = \{\underline{i}^{(j)}{}_1 . . 1 , \underline{i}^{(j)}{}_K\}$.

The induced voltage pattern resulting from the $k^{th}$ injected current pattern $\underline{i}^{(j)}{}_k$ at time $t_j$ is denoted as $\underline{u}^{(j)}{}_k = (u^{(j)}{}_{k1}, u^{(j)}{}_{k2}, \ldots, u^{(j)}{}_{kL})$, and the collection of all K measured voltage patterns observed at time $t_j$ is denoted as $\underline{U}^{(j)} = \{\underline{u}^{(j)}{}_1, \ldots, \underline{u}^{(j)}{}_K\}$.

At each time $t_j$, $j=1, \ldots, J$, the measured electric potentials depend on both the conductivity distribution and the injected current patterns according to electromagnetic physical laws which are represented symbolically by $$\underline{U}^{(j)} = f[\sigma^{(j)}(\underline{r},t_j),\underline{I}^{(j)}], j=1, \ldots, J \quad (13a)$$

Finally, the J measurement times can be combined with the collection of all of the injected currents denoted as $\underline{I} = \{\underline{I}^{(1)}, \ldots, \underline{I}^{(J)}\}$, and the collection of all of the resulting voltage measurements denoted as $\underline{U} = \{\underline{U}^{(1)}, \ldots, \underline{U}^{(J)}\}$. In terms of these combined sets of data, the relation between $\underline{U}$ and the conductivity $\sigma(\underline{r},t)$ satisfies electromagnetic physical laws denoted symbolically as $$\underline{U} = F[\sigma(\underline{r},t),\underline{I}] \quad (13b)$$

In order to obtain images of the electrical impedance distribution of the formation, known currents $\underline{I}$ are injected into the formation, and resulting electrode voltages $\underline{U}$ are measured. Given $\underline{I}$ and $\underline{U}$, the problem is to solve for the time-varying conductivity distribution $\sigma(\underline{r},t)$. A number of approaches to the static problem (no changes over time) have been studied for medical and nondestructive materials evaluation (see, e.g., Cheney, et al., "NOSER: An Algorithm for Solving the Inverse Conductivity Problem" *Intl. Journal Imaging Systems and Technology*, Vol. 2, pp 66–75 (1990); and Eggleston, et al., "The Application of Electric Current computed Tomography to Defect Imaging In Metals" *Review of progress in Quantitative NDE*, (Plenum Press, New York, 1989)). These solutions typically involve an iterative algorithm to identify a candidate conductivity distribution $\sigma(\underline{r})$ such that error between the actual measured set of electrode voltages $\underline{U}$ and those predicted using the model $F[\sigma(\underline{r}),\underline{I}]$ is minimized. Extending these static problem solutions to the time-varying conductivity distribution requires that the problem be viewed as a series of snapshots which are preferably linked over time such that the results of each previous snapshot imposes starting constraints on the system.

As with the reverse situation where the voltage is impressed and the current is measured, where the current is injected and the voltage is measured additional information is desired in order to provide a more robust solution to the time-varying conductivity problem set forth above. Again, for the provided tool, this additional information is obtained from the characteristics of the dynamic fluid flow as set forth above. Thus, equations (4)–(9) above, and the discussion used in conjunction with those equations applies. In addition, FIGS. 8a and 8b and the discussion above with respect to those figures applies, except that the EM model utilizes known current patterns $\underline{I}$, and compares predicted voltages $\underline{V}_{pred}$ against measured voltages $\underline{U}$, rather than using known voltages and measured currents. Regardless, the general iterative minimization techniques for solving for the unknowns is preferably the same.

Figure 9:
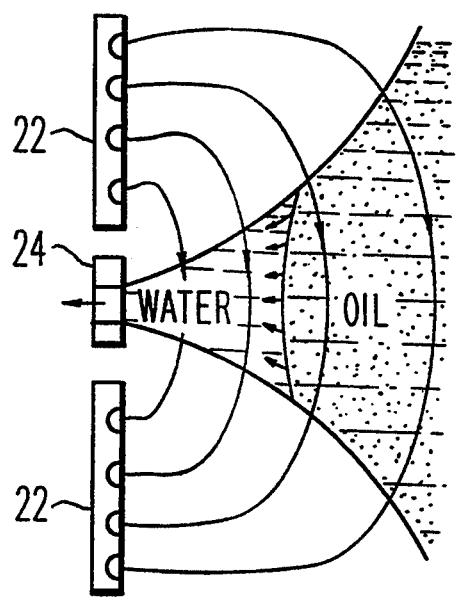
FIG. 9 is a schematic representation of a water/oil interface in a formation against which the preferred tool of the invention is placed.

Because of the number of unknowns in the above-described conductivity models, the number of measurements that would be required, and the considerable processing power required, it may be desirable to limit the conductivity determination from an arbitrary conductivity distribution to a simple conductivity profile; i.e., it may be desirable to consider only a simple conductivity profile such as a formation having oil-saturated and water-saturated zones defined by an interface as shown in FIG. 9. Rather than attempting to determine conductivity $\sigma(\underline{r})$ everywhere (for many values of $\underline{r}$), it is sufficient for many applications to determine only a small number of parameters of the conductivity model, such as the parameters defining the position of the oil-water interface. If "z" denotes the parameters for such a model, then conductivity throughout the modified volume $\sigma(r)$ may be expressed as a simple function of z:

$$\sigma(r) = C(z) \quad (14)$$

where C is a model which describes conductivity in terms of one or more parameters. The inversion problem then reduces to determining values of the parameters z from the predictive model $\underline{I}_{pred} = E[\sigma(\underline{r}), \underline{U}]$ as previously discussed.

Figure 10:
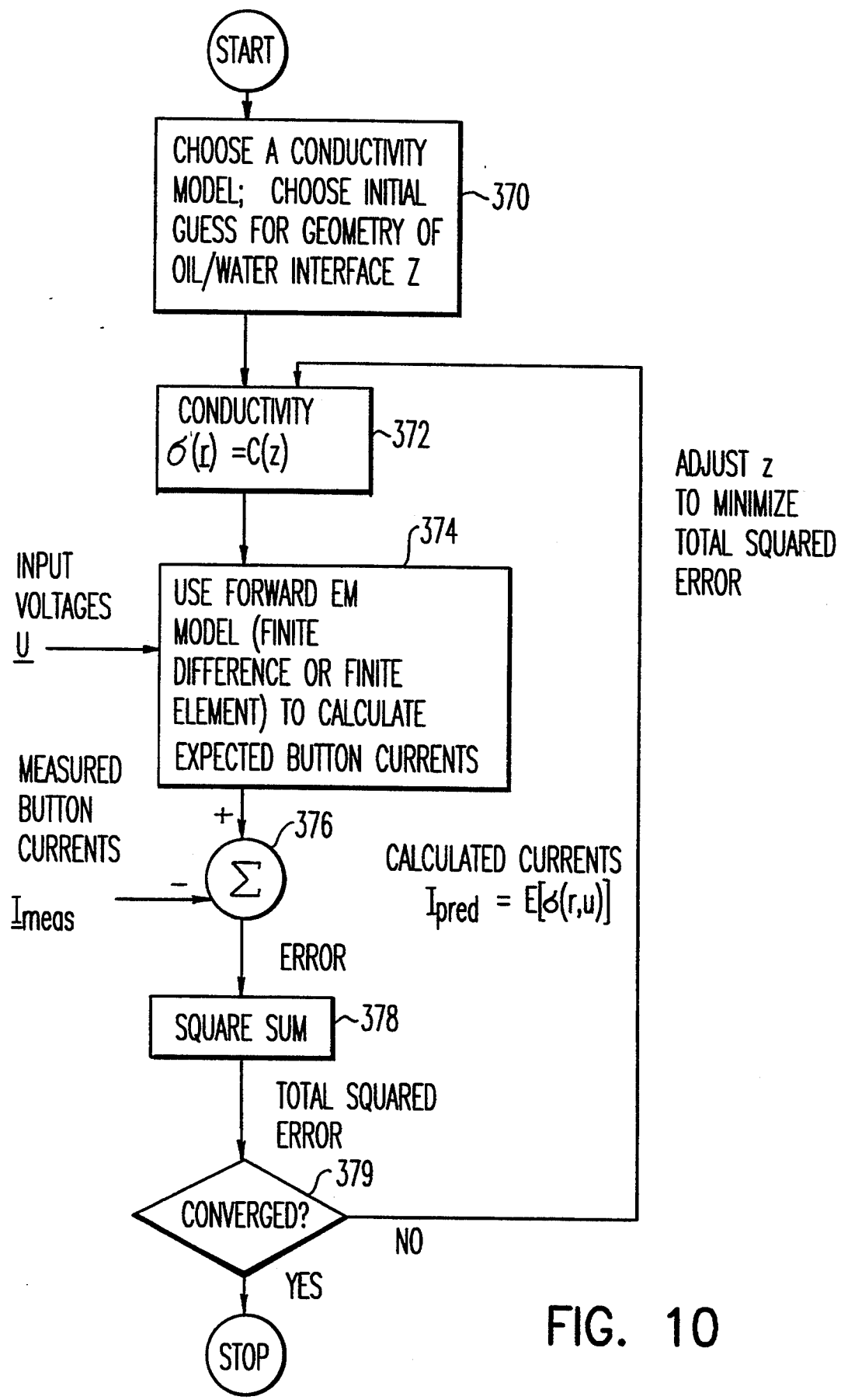
FIG. 10 is a flow chart for solving for the water/oil interface of FIG. 9 by utilizing electromagnetic measurements.

The preferred procedure for solving the inversion problem is seen in FIG. 10, where at step 370, a model such as that set forth in FIG. 9 is chosen, and values for an initial set of geometry variables $x_0$ are provided. As indicated at step 372, the initial guess for the conductivity is $\sigma(r) = C(z_0)$. The predicted set of button currents is then found at 374 using an electromagnetic model $\underline{I}_{pred} = E[\sigma(\underline{r}), \underline{U}]$. At 376, the predicted button currents are compared with the measured button currents $\underline{I}$, and the squared error is minimized at 378 and 379 using an optimization procedure (e.g., Newton's method, steepest descent, conjugate gradient, etc.) until convergence. It is of note, however, that the variables adjusted during optimization are those in z, rather than an arbitrary conductivity distribution $\sigma(\underline{r})$.

Figure 11A:
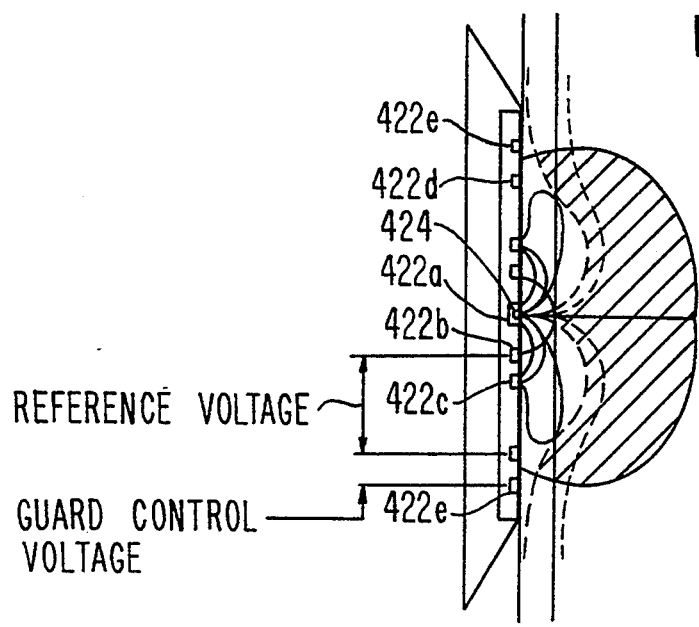
FIGS. 11a and 11b are side and front views respectively of a preferred integrated hydraulic probe and actively focussed electrode probe arrangement in accord with a second embodiment of the invention.
Figure 11B:
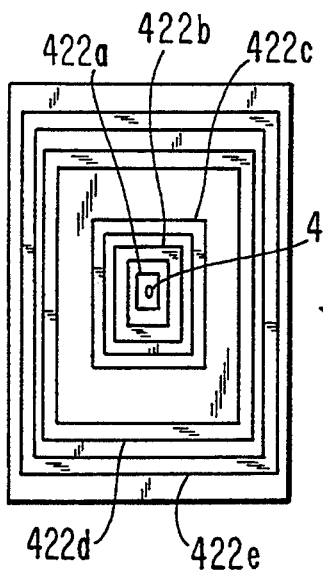

Turning to FIGS. 11a and 11b, and in accord with the current injection embodiment of the invention, a probe utilizing actively focused electrodes is provided. In the probe 400 of FIG. 11, a central hydraulic probe 424 is provided, and five electrodes 422a, 422b, 422c, 422d and 422e are concentrically therearound. Electrode 422a is a current injection electrode. Electrodes 422b and 422d are reference voltage electrodes for measuring a reference voltage therebetween. Electrode 422c is a current return electrode which is used to keep most of the current from the current injection electrode 422a from traveling in the mudcake and reentering the borehole without traveling through the formation. This is done by causing the potential between electrodes 422d and 422e to be zero.

While a hydraulic probe 424 is shown with rectangular electrodes, it will be appreciated that other configurations for the electrodes (e.g., square, circular, etc.) could be utilized. However, it is preferable for the electrodes to have identical shapes with the concentric center being the hydraulic probe.

Figure 12:
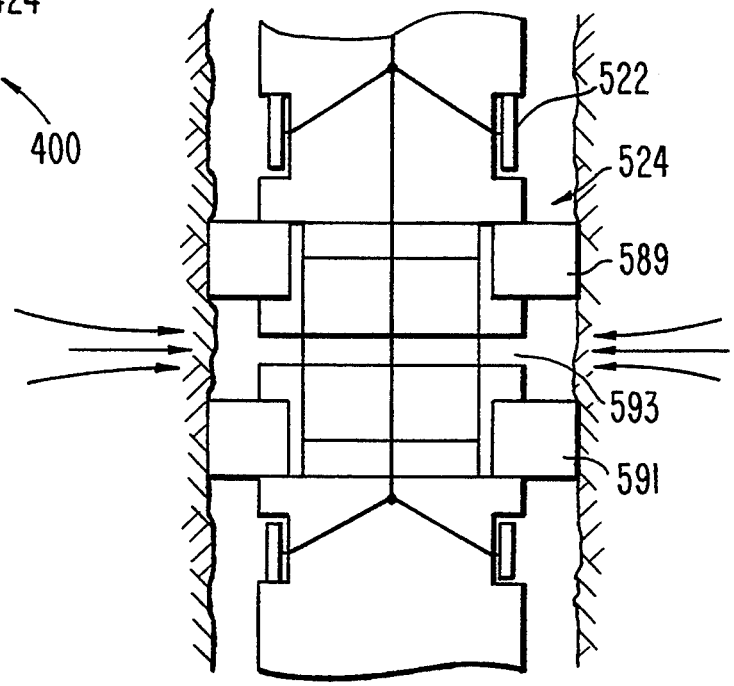
FIG. 12 is a cross-sectional view of alternative hydraulic and electromagnetic probe arrangement.

While the hydraulic probes described with reference to the above embodiments are essentially point sources or sinks, it will be appreciated that a "two-dimensional" hydraulic probe can be provided such as shown in FIG. 12. In FIG. 12, hydraulic probe 524 includes two straddle packers 589 and 591 which straddle a three hundred sixty degree port opening 593 in the tool. When the tool is moving, the straddle packers are not inflated. However, when the tool is set in a desired location, the straddle packers 589 and 591 are inflated as shown in FIG. 12 so that they are in contact with the formation walls, and port opening 593 is resultingly in fluid communication with the formation as opposed to the borehole. As indicated in FIG. 12, the electrodes 522 are separately extendable, and may be retracted as shown in FIG. 12, or extended into contact with the formation.

There have been described and illustrated herein borehole tools and methods for making electromagnetic, permeability and other measurements of earth formations. While particular embodiments have been described, it is not intended that the invention be limited thereby, as it is intended that the invention be as broad in scope as the art will allow. Thus, while particular types and arrangements of hydraulic and electromagnetic devices were described, it will be appreciated that other device types and arrangement could be utilized to provide desired information. Also, while a preferred method of integrating the measurements of the electromagnetic and hydraulic devices was set forth, it will be appreciated that other models and methods of using the measurements, separately, or together will present themselves to those skilled in the art. It will therefore be appreciated by those skilled in the art that yet other modifications could be made to the provided invention without deviating from its spirit and scope as so claimed.

We claim:

1. Apparatus for the investigation of an earth formation transverse by a borehole, comprising:

a) a plurality of electrode means for making electrical contact with a segment of a wall of said borehole and for making electrical measurements relating to an electromagnetic investigation of said earth formation adjacent said segment of said borehole wall;

b) hydraulic port means for making hydraulic contact with said formation;

c) flow means coupled to said hydraulic port for accomplishing at least one of injecting fluid into said formation and withdrawing fluid from said formation via said hydraulic port;

d) hydraulic property measurement means for determining pressures at said hydraulic port during withdrawal of fluid from said formation or during injection of fluid into said formation, wherein, said plurality of electrode means make said electrical measurements during said withdrawal of fluid from said formation or during said injection of fluid into said formation, and said hydraulic port means is sufficiently adjacent said plurality of electrode means such that said electrical measurements are impacted by said withdrawal of fluid or said injection of fluid.

2. Apparatus according to claim 1, wherein:
said plurality of electrode means and said hydraulic port means are located on a single probe means which laterally extends from said apparatus, wherein said plurality of electrode means comprises an actively focussed electrode means with concentric electrodes, and said hydraulic port means is located concentrically and central said concentric electrodes.

3. Apparatus according to claim 1, wherein:
said hydraulic port means comprises first and second inflatable straddle packers longitudinally displaced from each other along said apparatus, said inflatable straddle packers when inflated forming hydraulic seals azimuthally around said borehole and defining a hydraulic port in fluid communication with said formation.

4. Apparatus according to claim 1, further comprising:
e) processing means coupled to said hydraulic property measurement means and said plurality of electrode means for determining at least one hydraulic or electromagnetic characteristic of said formation.

5. Apparatus according to claim 4, wherein:
said processing means determines said at least one hydraulic or electromagnetic characteristic according to an equation $$\underline{I} = E[h(\underline{x},\underline{y}), \underline{U}]$$

where $\underline{I}$ are current measurements comprising said measurements made by said electrode means, $\underline{U}$ are known voltages impressed by said electrode means onto said formation, $\underline{y}$ are known values for a second set of formation characteristics, $\underline{x}$ is said at least one hydraulic or electromagnetic unknown characteristic, h is a function which relates the input formation variables $\underline{x}$ and $\underline{y}$ and the spatial distribution of formation conductivity according to a fluid mechanical and petrophysical model, and E is a function which maps the spatial distribution of formation conductivity and the known voltages $\underline{U}$ to said measurements $\underline{I}$.

6. Apparatus according to claim 5, wherein:
said processing means predicts current measurements $\underline{I}_{pred}$ based on said equation, compares said predicted measurements with said measurements, and minimizes differences between said predicted measurements and said measurements to determine a value for said at least one characteristic.

7. Apparatus according to claim 4, wherein:
said processing means determines said at least one hydraulic or electromagnetic characteristic according to an equation $$\underline{U} = F[h(\underline{x},\underline{y}), \underline{I}]$$

where $\underline{U}$ are measured voltages comprising said measurements made by said electrode means, $\underline{I}$ are known currents injected by said electrode means into said formation, $\underline{y}$ are known values for a second set of formation characteristics, $\underline{x}$ is said at least one unknown hydraulic or electromagnetic characteristic, h is a function which the relates the input formation variables $\underline{x}$ and $\underline{y}$ and the spatial distribution of formation conductivity according to a fluid mechanical and petrophysical model, and F is a function which maps the spatial distribution of formation conductivity and the known currents $\underline{I}$ to said measurements $\underline{U}$.

8. Apparatus according to claim 7, wherein:
said processing means predicts measurements $\underline{U}_{pred}$ based on said equation, compares said predicted measurements with said measurements, and minimizes differences between said predicted measurements and said measurements to determine a value for said at least one unknown characteristic.

9. Apparatus according to claim 1, wherein:
said plurality of electrode means are located on a first laterally extending pad means, and
said hydraulic port means is located on a second laterally extending pad means substantially adjacent said first laterally extending pad means.

10. Apparatus according to claim 9, wherein:
a single probe means of said apparatus includes said first and second laterally extending pad means, said single probe means having means for urging said probe into contact with said formation.

11. Apparatus according to claim 10, further comprising:
spring bias means coupled to each first laterally extending pad means for limiting the setting force of said first laterally extending pad means when said probe is urged into contact with said formation by said means for urging.

12. Apparatus according to claim 10, wherein:
said apparatus includes first and second of said probe means, said first probe means being azimuthally displaced from said second probe means around said apparatus.

13. Apparatus according to claim 10, wherein:
said apparatus includes first and second of said probe means, said first probe means being longitudinally displaced from second probe means along said apparatus.

14. Apparatus according to claim 13, wherein:
said apparatus includes a third said probe means, said third probe means being azimuthally displaced from said first probe means.

15. A method for investigating an earth formation with a borehole tool having a plurality of electrode means for making electrical contact with a segment of a wall of said borehole and for making measurements relating to an electromagnetic investigation of said earth formation adjacent said segment of said borehole wall, a hydraulic port means substantially adjacent said plurality of electrode means for making hydraulic contact with said formation, a flow means coupled to said hydraulic port means for injecting fluid into said formation and/or for withdrawing fluid from said formation via said hydraulic port means, and hydraulic property measurement means for determining pressures at said hydraulic probe before, during, or after withdrawal or injection of fluid from said formation, said method comprising:

a) determining a depth at which said borehole tool is to be set;

b) lowering or raising said borehole tool to approximately said depth;

c) scanning said formation with said plurality of electrode means to provide first electromagnetic images of said formation at a plurality of different depths near said depth;

d) using said first electromagnetic images to determine exactly where to set said borehole tool;

e) setting said borehole tool with said hydraulic port means at exactly a determined location; and f) with said flow means, withdrawing fluid from and/or injecting fluid into said formation via said hydraulic port means with said hydraulic port means set at exactly said determined location.

16. A method according to claim 15, wherein:
said step of determining a depth at which said borehole tool is to be set comprises obtaining second electromagnetic images of said formation, and locating depths of interest based on said second electromagnetic images.

17. A method according to claim 16, wherein:
said second electromagnetic images of said formation are obtained by said borehole tool.

18. A method according to claim 15, wherein:
said step of determining a relative depth at which said borehole tool is to be set comprises obtaining information regarding strata of said formation and their depths in said formation from a second borehole tool.

19. A method according to claim 15, wherein:
said step of using said first electromagnetic images further comprises comparing said second electromagnetic images with said first electromagnetic images.

20. A method according to claim 15, further comprising:

g) while withdrawing fluid from or injecting fluid into said formation via said hydraulic port means, scanning said formation with said plurality of electrode means to provide a plurality of electromagnetic images of said formation adjacent said hydraulic port means over time.

21. A method for investigating an earth formation with a borehole tool having a plurality of electrode means for making electrical contact with a segment of a wall of said borehole and for making measurements relating to an electromagnetic investigation of said earth formation adjacent said segment of said borehole wall, a hydraulic port means substantially adjacent said plurality of electrode means for making hydraulic contact with said formation, a flow means coupled to said hydraulic port means for injecting fluid into said formation and/or for withdrawing fluid from said formation via said hydraulic port means, and hydraulic property measurement means for determining at least pressures at said hydraulic probe before, during, or after withdrawal or injection of fluid from said formation, said method comprising:

a) setting said borehole tool at a depth in said formation;

b) with said flow means, withdrawing fluid from or injecting fluid into said formation via said hydraulic port means;

c) scanning said formation with said plurality of electrode means to provide electromagnetic information regarding said formation at said depth at two different times, a first of said two different times being either before or at a first time during said fluid injection or withdrawal, and a second of said two different times being either at a second time different from said first time during said fluid injection or withdrawal or after said fluid injection or withdrawal.

22. A method according to claim 21, wherein:
said step of scanning said formation comprises scanning said formation at a plurality of times during fluid injection into or withdrawal from said formation.

23. A method according to claim 21, further comprising:
upon withdrawing fluid from or injecting fluid into said formation, making measurements with said hydraulic property measurement means, and from said measurements of said hydraulic property measurement means and said electromagnetic information measured by said plurality of electrode means, determining a value for at least one characteristic of said formation. second set of formation characteristics, $\underline{x}$ is said at least one unknown hydraulic or electromagnetic characteristic, h is a function which the relates the input formation variables $\underline{x}$ and $\underline{y}$ and the spatial distribution of formation conductivity according to a fluid mechanical and petrophysical model, and F is a function which maps the spatial distribution of formation conductivity and the known currents $\underline{I}$ to said measurements $\underline{U}$.

24. A method according to claim 23, wherein
from said electromagnetic information regarding said formation at said depth at said two different times, determining said at least one characteristic of said formation according to an equation $$\underline{I} = E[h(\underline{x},\underline{y}), \underline{U}]$$

where $\underline{I}$ are current measurements and comprise said electromagnetic information provided by said electrode means, $\underline{I}$ are known currents injected by said electrode means into said formation, $\underline{y}$ are known values for a second set of formation characteristics, $\underline{x}$ is said at least one characteristic, h is a function which the relates the input formation variables $\underline{x}$ and $\underline{y}$ and the spatial distribution of formation conductivity according to a fluid mechanical and petrophysical model, and E is a function which maps the spatial distribution of formation conductivity and the known voltages $\underline{U}$ to said current measurements $\underline{I}$.

25. A method according to claim 23, wherein:
from said electromagnetic information regarding said formation at said depth at said two different times, determining said at least one characteristic of said formation according to an equation $$\underline{U} = F[h(\underline{x},\underline{y}), \underline{I}]$$

where $\underline{U}$ are voltage measurements and comprise said electromagnetic information provided by said electrode means, $\underline{I}$ are known currents injected by said electrode means into said formation, $\underline{y}$ are known values for a second set of formation characteristics, $\underline{x}$ is said at least one characteristic, h is a function which relates the input formation variables $\underline{x}$ and $\underline{y}$ and the spatial distribution of formation conductivity according to a fluid mechanical and petrophysical model, and F is a function which maps the spatial distribution of formation conductivity and the known currents $\underline{I}$ to said voltage measurements $\underline{U}$.

* * * * *